United States Patent [19]

Rudloff

[11] Patent Number: 4,664,100
[45] Date of Patent: May 12, 1987

[54] PENILE IMPLANT

[76] Inventor: David A. C. Rudloff, 330 E. Hibiscus, Melbourne, Fla. 32901

[21] Appl. No.: 672,689

[22] Filed: Nov. 19, 1984

[51] Int. Cl.⁴ .............................................. A61F 5/00
[52] U.S. Cl. ...................................................... 128/79
[58] Field of Search .................................. 128/79, 1 R

[56] References Cited

U.S. PATENT DOCUMENTS

| | | | |
|---|---|---|---|
| 2,417,850 | 3/1947 | Winslow | 361/207 |
| 4,201,202 | 5/1980 | Finney et al. | 128/79 |
| 4,498,466 | 2/1985 | Pomeranz | 128/79 |

Primary Examiner—Gene Mancene
Assistant Examiner—Cary E. Stone
Attorney, Agent, or Firm—Antonelli, Terry & Wands

[57] ABSTRACT

A method and apparatus for surgically implanting a penile prosthesis for the treatment of erectile impotence. This is accomplished by surgically implanting two separate penile implants each comprising an elongated receptacle containing an electro-rheological fluid; electrodes positioned along the elongated receptacle, so that the electro-rheological fluid is interposed between the electrodes; and, e.g., a power source for applying a potential difference across the electrodes wherein the change in viscosity of the electro-rheological fluid contained in the elongated receptacle is directly proportional to the change in potential difference across the electrodes. As the potential difference across the electrodes increases, the viscosity of the electro-rheological fluid increases and the elongated receptacle becomes more rigid, thus a penile erection is accomplished. The elongated receptacle may also be attached to a flexible reservoir to regulate the supply of electro-rheological fluid contained in the elongated receptacle.

18 Claims, 7 Drawing Figures

PENILE IMPLANT

BACKGROUND OF THE INVENTION

The present invention relates to methods and devices for enabling human adult males to achieve penile erections, and particularly by use of an electro-rheological fluid as a hardening means.

It has been known to use penile implants in order to assist otherwise impotent individuals in achieving penile erections. Most of the known devices insert tubes or receptacles into the penis and supply fluid thereto by means of a reservoir. However, these devices result in malfunctions due to leakage of fluid out of the receptacle and clogging due to the valves used to control the flow of fluid between the receptacle and the reservoir. These problems result in great discomfort and annoyance to the implantee.

U.S. Pat. No. 4,201,202 discloses a penile implant including an elongated, flexible rod having a short, proximal portion of relatively stiff material which is adapted to be implanted into the root end of the corpus cavernosum to support the implant and a longer distal portion of softer and more flexible material adapted to be implanted in the corpus cavernosum of the pendulus penis. A flexible cylindrical sleeve is positioned around the rod in a fluid-tight manner forming a chamber for receiving pressurized fluid. Furthermore, it includes a pressure bulb for pressurizing fluid, tubing communicating between the chamber and the pressure bulb, and valve means for controlling the flow of the pressurizing fluid between the pressure bulb and the chamber. The flexible cylindrical sleeve is pressurized upon receiving fluid from the pressure bulb to rigidize the implant and to effect a penile erection.

U.S. Pat. No. 3,853,121 discloses an elongated flexible elastic tube which is implanted in the penis together with a flexible container which contains a fluid to be transferred from the container into the tube when the container is compressed so that the fluid thus displaced in the tube will elongate the latter and render the tube relatively rigid so that in this way it is possible to achieve a penile erection.

Neither of the aforementioned U.S. patents assist in overcoming the disadvantages of fluid leakage and the resultant reduction in the size and duration of the penile erection. The present invention overcomes the aforementioned disadvantages as well as provides a new and novel method and device for obtaining a penile erection.

SUMMARY OF THE INVENTION

It is the primary object of the present invention to provide a method and device which will enable an otherwise impotent individual to obtain a penile erection.

Thus, it is an object of the present invention to provide a method and device which will enable an individual to achieve a penile erection by means of an electro-rheological fluid. It is also an object of the present invention to provide a method and device which will maintain a penile erection without fluid leakage, valve cloggage or resulting reduction in size and duration of a penile erection.

It is also an object of the present invention to provide a method and device which will enable an individual to achieve a penile erection by regulating a power source to cause a potential difference across opposing electrodes positioned along either side of an elongated receptacle to cause the viscosity of an electro-rheological fluid interposed between those electrodes to change in direct proportion to the change in potential difference across the electrodes, whereby the electro-rheological fluid becomes rigid as the potential difference increases.

According to the present invention, an elongated receptacle is inserted into a corpus cavernosum of the penis, with an electro-rheological fluid being contained in the receptacle. Electrodes are attached to the elongated receptacle so that the electro-rheological fluid is interposed between the electrodes and where the electrodes are opposite one another so that an electric field is created when an electric current passes through the electrodes. The electrodes are connected to a means for causing a potential difference across the electrodes, wherein the change in viscosity of the electro-rheological fluid, which is contained in the elongated receptacle, is directly proportional to the change in potential difference across the electrodes. Accordingly, when the potential difference across the electrodes increases, the viscosity of the electro-rheological fluid also increases. An increased potential difference across the electrodes will cause the electro-rheological fluid to become rigid, thus resulting in a penile erection. The rigidity properties of electro-rheological fluids are well known as disclosed in U.S. Pat. Nos. 4,444,298; 2,417,850; British Pat. Nos. 1,501,635; and 1,570,234. In particular, U.S. Pat. Nos. 4,444,298 and 2,417,850 demonstrate the use of electro-rheological fluids in electrically controlled clutches.

The present invention may also include many additional features which shall be further described below.

DESCRIPTION OF THE PREFERRED EMBODIMENT

Figure 1:
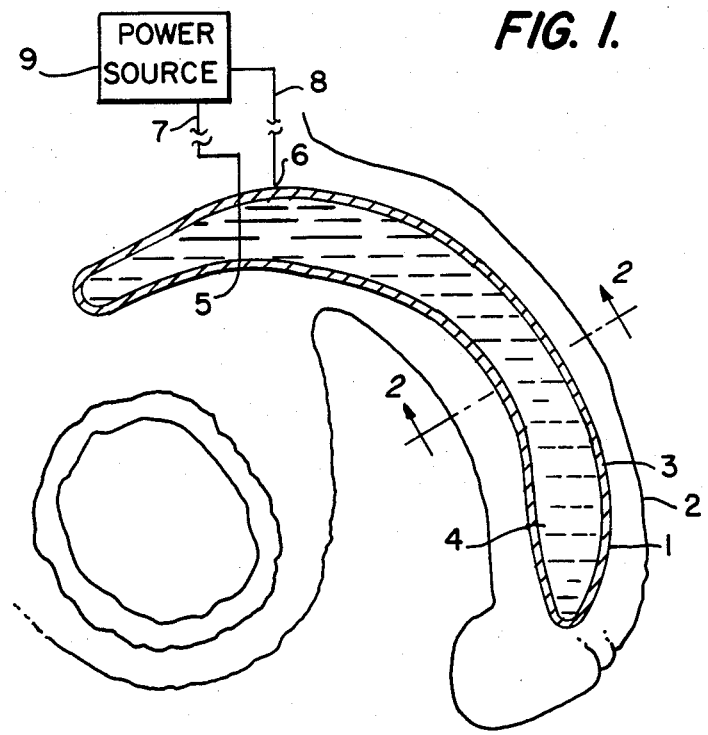
FIG. 1 is a sectional view of the penile implant of the present invention in a non-rigid state.
Figure 8:
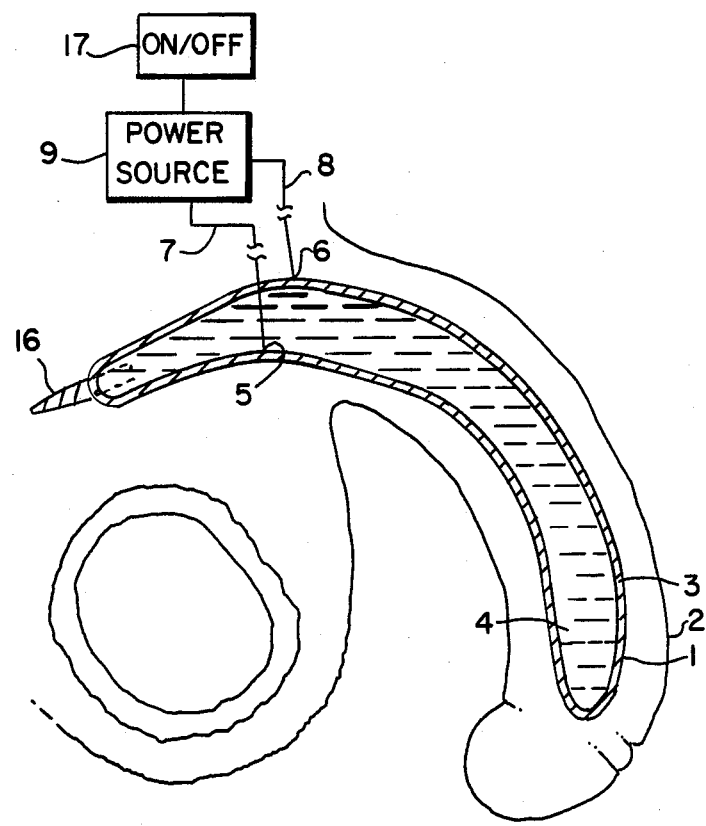
FIG. 8 is a sectional view of another embodiment of the present invention.

FIG. 1 describes the penile implant according to the present invention. In particular, the penile implant 1 is implanted longitudinally in penis 2. The penile implant 1 comprises an elongated receptacle 3 which contains an electro-rheological fluid 4 therein. Electrodes 5 and 6 which are connected to a power source via insulated electrical wires 7 and 8, are positioned along the elongated receptacle 3 so that the electro-rheological fluid 4 is interposed between electrodes 5 and 6 and wherein electrodes 5 and 6 are opposite one another so as to create an electric field when an electric current passes through them. The power source 9 can be positioned or implanted anywhere on or in the body of the human where it is accessible for switching on and off. Additionally, the power source may include a magnetic on-off switch 17, as shown in FIG. 8, which may be operated externally by means of a magnet. When the power source 9 is switched to the on position, a current is passed through the electrical wires 7 and 8 to electrodes 5 and 6, so that a potential difference is caused across electrodes 5 and 6, wherein the viscosity of the electro-rheological fluid 4 contained in the elongated receptacle 3 and interposed between electrodes 5 and 6 is increased in direct proportion to the increase in potential difference across the electrodes 5 and 6. However, before activating the power source 9, it is preferable to position the penis in the direction of the preferred erection, since the electro-rheological fluid 4 becomes hard upon receipt of a minimum potential difference across electrodes 5 and 6 so that the electro-rheological fluid 4 will take the shape of the elongated receptacle 3 once the minimum potential difference across electrodes 5 and 6 is generated from power source 9. Furthermore, electrodes 5 and 6 are used simply for schematic purposes, since this invention envisions the use of any conventional type of electrode apparatus for creating the electric field necessary for making the electro-rheological fluid hard.

Figure 2:
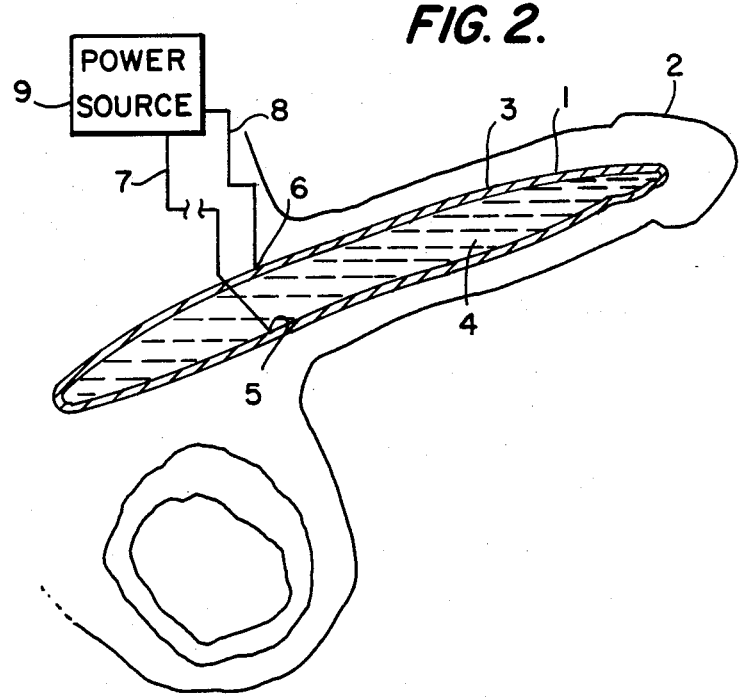
FIG. 2 is a sectional view of a penile implant according to the present invention in the rigid state.

FIG. 2 demonstrates a preferred shape of the elongated receptacle 3 when the power source 9 is activated to cause a potential difference across electrodes 5 and 6, wherein the electro-rheological fluid 4 becomes rigid. However, the penis may be positioned manually so that the elongated receptacle 3 may be made rigid in most any direction. Similarly, when the power source 9 is placed in the "off" position, the electro-rheological fluid 4 takes on a non-rigid state and permits fairly normal functioning of the penis 2.

The electro-rheological fluid 4 comprises a slurry of a finely divided hydrophilic solid and hydrophobic liquid. These fluids undergo flow property variations when subjected to electric fields, such that in the absence of an electric field these fluids behave in a "Newtonian" fashion but, when an electric field is applied, the fluids behave approximately as a "Bingham plastic". The present invention envisions the use of any known electro-rheological fluid. Preferably, an electro-rheological fluid which includes an oil having a specific gravity of 0.8 to 1.4 and which contains polymethacrylic particles of 10 microns in diameter, and with a specific gravity of 1.4, suspended in the oil.

Figure 7:
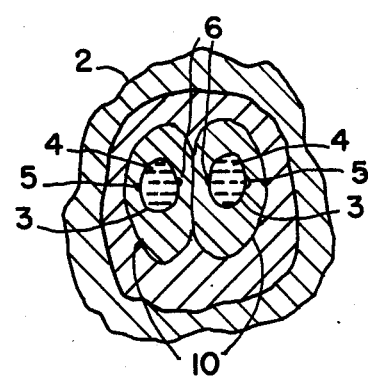
FIG. 7 is a cross sectional view taken along the lines 2—2 of FIG. 1.

The elongated receptacle 3 is constructed of a silicone-coated fabric such that it is fluid-tight. Also, the elongated receptacle 3 is inserted into the corpus cavernosum 10 as shown in FIG. 7 wherein the corpus cavernosum traverses the entire length of the penis so that the elongated receptacle 3 is positioned longitudinally along the penis. Each penis contains two corpus cavernosums 10, and accordingly, it is preferable that each surgical implant includes two elongated receptacles with either a single power source 9 or dual power sources. The elongated receptacle 3 may also include a support rod 16, as shown in FIG. 8, located at the end portion of the elongated receptacle 3 at the point furthest from the tip of the penis 4, so that the support rod 16 is implanted into the root end of the corpus cavernosum to support the elongated receptacle 3. Furthermore, it is preferable that electrodes 5 and 6 span the entire length of the elongated receptacle 3 wherein all of the electro-rheological fluid 4 contained in elongated receptacle 3 is positioned within the electric field created when an electric current is passed through electrodes 5 and 6.

Figure 3:
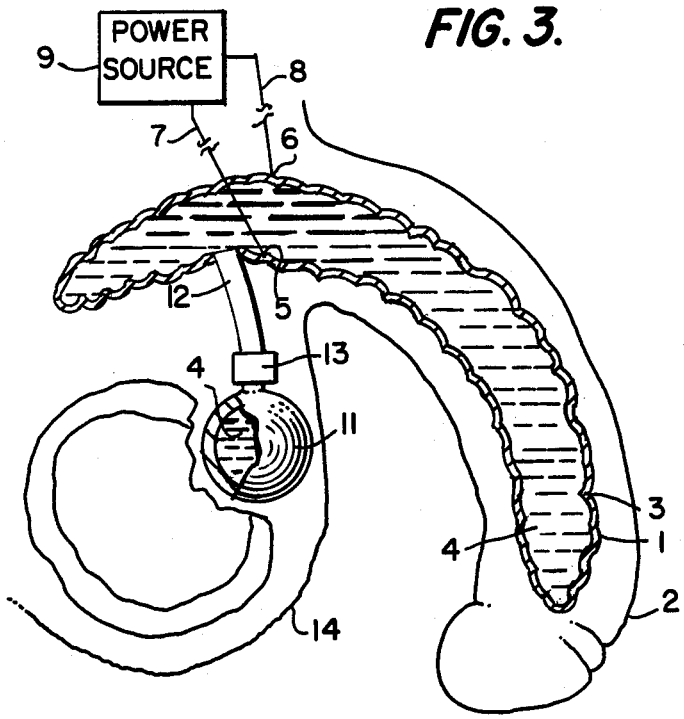
FIG. 3 is a sectional view of another embodiment of the present invention which includes a flexible reservoir filled with electro-rheological fluid.

FIG. 3 demonstrates an additional embodiment of the present invention including a flexible reservoir 11 which contains electro-rheological fluid 4 and is connected to the elongated receptacle 3 by means of conduit 12 and valve 13. Here, the reservoir 11 is preferably constructed of a flexible silicone material, such as the material used for making the elongated receptacle 3. The valve 13, which is interposed between reservoir 11 and conduit 12, is used for controlling the flow of electro-rheological fluid 4 between the reservoir 11 and elongated receptacle 3. The valve 13 may be of any suitable type adapted for controlling the flow of liquid, preferably a normally closed valve which is opened manually by squeezing the valve body or the reservoir and which can either be closed by additional manipulation or which sufficiently delays return of the electro-rheological fluid 4 to the reservoir 11.

In the embodiment shown in FIG. 3, the elongated receptacle 3 is in a collapsed position and most of the electro-rheological fluid is contained in reservoir 11. The conduit 12 can be constructed of the same material as that of the elongated receptacle 3. Moreover, receptacle 11, valve 13 and conduit 12 can normally be implanted into the scrotum 14. In the case where penile implants are surgically implanted into each of the corpus cavernosum 10, it is preferable that each penile implant 1 contain its own fluid reservoir 11.

In accordance with FIG. 3, the electro-rheological fluid 4 is supplied from reservoir 11 through valve 13 and conduit 12 into the elongated receptacle 3 so that elongated receptacle 3 is no longer in a collapsed position, and the penis 2 becomes distendible as a result of the flowing of the electro-rheological fluid 4 into elongated receptacle 3. Thereafter, the power source 9 is switched to the "on" position so that a potential difference occurs between electrodes 5 and 6, so that the electro-rheological fluid 4 becomes rigid resulting in a penile erection.

The collapsed state of the elongated receptacle 3 as depicted in FIGS. 1 and 3 results simply by returning the power source to the "off" position and either opening valve 3 or permitting the liquid to flow under gravity from the elongated receptacle 3, through conduit 12 and valve 13, into reservoir 11. The increase in viscosity of the electro-rheological fluid when there is an increase in the potential difference between electrodes 5 and 6 also prevents leakage of fluid from the elongated receptacle 3 back into reservoir 11 due to the rigid state of the electro-rheological fluid.

Figure 4:
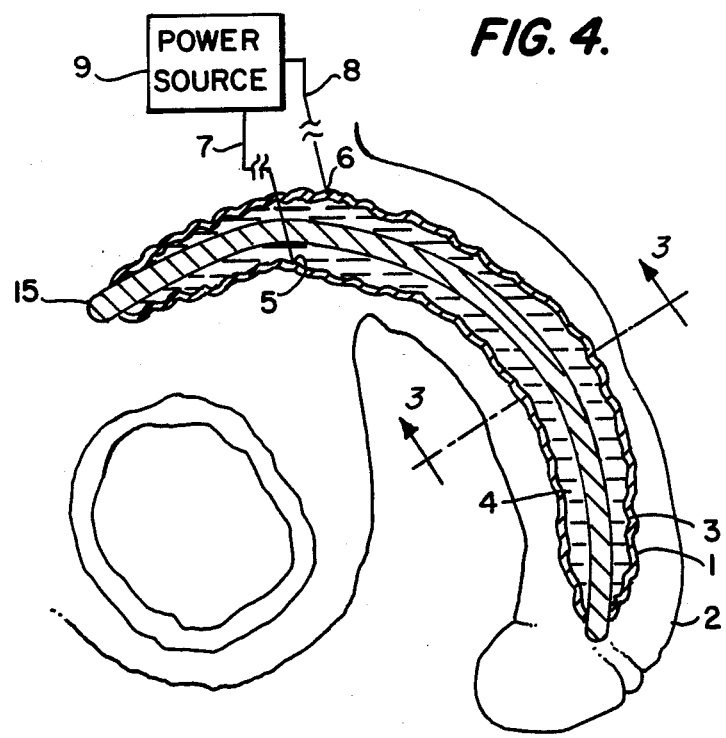
FIG. 4 is a sectional view of another embodiment of the present invention, wherein an elongated flexible rod is longitudinally positioned in the elongated receptacle.
Figure 6:
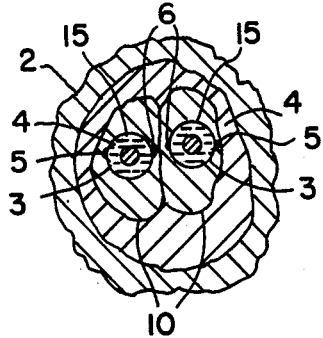
FIG. 6 is a cross sectional view taken along the lines 3—3 of FIG. 4.

The penile implant 1 may also include an elongated flexible rod 15, where the rod 15 has one end inserted into the root end of the corpus cavernosum to support the implant such that the remainder of the rod 15 is adapted to be implanted into the corpus cavernosum 10 of the penis 1. FIG. 4 demonstrates that the rod 15 is centrally and logitudinally positioned through the elongated receptacle 3. More particularly, the elongated receptacle 3 is positioned axially about the intermediate section of the rod 15 and is sealed at each end of the rod 15 in a fluid-tight manner to form a chamber for the electro-rheological fluid 4. Similar to the description of FIGS. 1 and 2, the penile implant 1 in FIG. 4 has electrodes 5 and 6 positioned along the elongated receptacle wherein the electro-rheological fluid 4 is interposed between those electrodes so that when the power source 9 is switched to the "on" position the electro-rheological fluid 4 becomes rigid and results in a penile erection. Moreover, FIG. 6 depicts the cross sectional view along lines 3—3 of FIG. 4, which shows two penile implants 1 inserted into both corpus cavernosums 10 of the penis 2.

Figure 5:
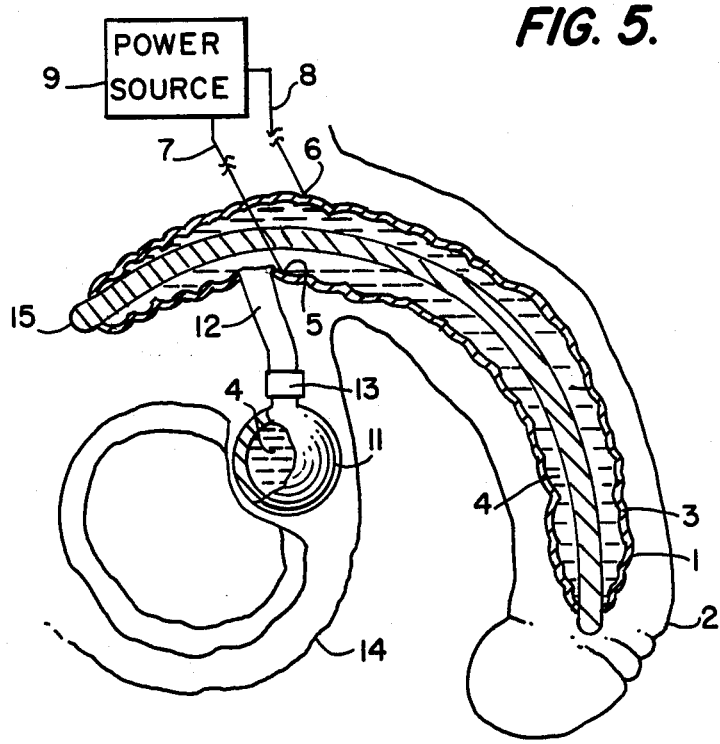
FIG. 5 is a sectional view of another embodiment according to the present invention which shows the penile implant of FIG. 4 attached to a flexible reservoir.

FIG. 5 refers to an additional embodiment to FIG. 4, wherein a reservoir 11 is connected to the elongated reservoir 3 through valve 13 and conduit 12. FIG. 5 demonstrates a penile implant 1 wherein the elongated receptacle 3 is in a collapsed position and wherein electro-rheological fluid 4 is primarily contained in reservoir 11. The apparatus according to FIG. 5 is used by passing the electro-rheological fluid 4 from the reservoir 11 through valve 13 and conduit 12 into the elongated receptacle 3 resulting in a distendible penis 2. Thereafter, an electrical current is passed through electrodes 5 and 6, and the electro-rheological fluid 4 becomes rigid resulting in a penile erection.

It is also possible for the end portion of the elongated receptacle 3 nearest the root end of the corpus cavernosum to be inserted into the root end to act as a support for the entire penile implant 1. This would avoid any need for a more complicated penile implant as depicted in FIGS. 4 and 5 which use an elongated flexible rod 15 as the support.

Finally, FIG. 8 depicts another embodiment according to the present invention, wherein a support rod 16 extends outwardly from an end of the elogated receptacle 3 so that it may be implanted in the root end of the corpus cavernosum to support the penile implant 1.

What is claimed is:

1. A penile implant comprising:
   an elongated receptacle adapted to be inserted into the corpus cavernosum of the penis;
   an electro-rheological fluid being contained in said elongated receptacle, the receptacle containing sufficient electro-rheological fluid so as to result in a penile erection;
   electrodes positioned along said elongated receptacle, wherein said electro-rheological fluid is interposed between said electrodes; and
   means for applying a potential difference across said electrodes, whereby application of said potential difference across said electrodes causes said electro-rheological fluid to become rigid and enables a penile erection to be achieved.

2. A penile implant according to claim 1, wherein said electrodes are positioned opposite each other so that an electric field is created when said means for applying a potential difference is activated and whereby a majority of said electro-rheological fluid becomes rigid when said potential difference occurs across said electrodes.

3. A penile implant according to claim 2, wherein said electrodes extend the length of said elongated receptacle.

4. A penile implant according to claim 1, wherein said elongated receptacle has means for supplying electro-rheological fluid thereto and withdrawing said electro-rheological fluid therefrom.

5. A penile implant according to claim 4, wherein said means for supplying and withdrawing said electro-rheological fluid is a flexible reservoir.

6. A penile implant according to claim 5, wherein said flexible reservoir has means for regulating the flow of said electro-rheological fluid between said flexible reservoir and said elongated receptacle.

7. A penile implant according to claim 5, wherein said flexible reservoir is positioned so that said electro-rheological fluid can be withdrawn from said elongated receptacle by gravity.

8. A penile implant according to claim 5, wherein said flexible reservoir is adapted to be located in the scrotum.

9. A penile implant according to claim 1, wherein said elongated receptacle consists essentially of a silicone material.

10. A penile implant according to claim 1, wherein said electro-rheological fluid comprises polymethacrylic particles of 10 microns in diameter and a specific gravity of 1.4 suspended in an oil with a specific gravity of 0.8 to 1.4.

11. A penile implant according to claim 1, wherein said elongated receptacle includes an elongated flexible rod longitudinally and centrally positioned in said elongated receptacle wherein said elongated receptacle is fitted around said rod as a sleeve and is secured at both ends of said rod to create a fluid chamber therein.

12. A penile implant according to claim 11, wherein a portion of said rod is inserted into the root end of said corpus cavernosum and said elongated receptacle is fitted above the portion of said rod which is inserted in said corpus cavernosum.

13. A penile implant according to claim 12, wherein said rod is a silicone material.

14. A penile implant according to claim 1, wherein said elongated receptacle includes a support rod at the tip of said elongated receptacle whereby said support rod is implanted into the root end of said corpus cavernosum to support said implant.

15. A penile implant according to claim 1, wherein said means for applying a potential difference includes on/off switching means, for applying or not applying said potential difference, so that a penile erection can be achieved by applying said potential difference while fairly normal functioning of the penis can be achieved when the potential difference is not applied.

16. A method of achieving a penile erection using a penile implant containing an electro-rheological fluid contained in an elongated receptacle inserted in the corpus cavernosum of the penis, the receptacle containing sufficient electro-rheological fluid such that a penile erection can be achieved; wherein electrodes are connected along said elongated receptacle so that said electro-rheological fluid is interposed between said electrodes; including the step of applying a potential difference across said electrodes, so that said electro-rheological fluid becomes rigid and a penile erection is achieved.

17. A method of achieving a penile erection according to claim 16, including the further step of removing said potential difference so as to enable fairly normal functioning of the penis to be achieved.

18. A penile implant comprising:
   an elongated receptacle adapted to be inserted into the corpus cavernosum of the penis;
   an electro-rheological fluid being contained in said elongated receptacle;
   electrodes positioned along said elongated receptacle, wherein said electro-rheological fluid is interposed between said electrodes; and
   means for causing a potential difference across said electrodes, said means for causing a potential difference across said electrodes being a power source adapted to be implanted in the body of a human, said power source including a magnetic responsive on/off switch so that an exterior magnet may be used to activate or deactivate said potential difference across said electrodes, whereby said electrorheological fluid becomes rigid upon activation of the potential difference across said electrodes.

* * * * *